United States Patent [19]

Shanks et al.

[11] Patent Number: 4,978,503
[45] Date of Patent: Dec. 18, 1990

[54] DEVICES FOR USE IN CHEMICAL TEST PROCEDURES

[75] Inventors: Ian A. Shanks; Alan M. Smith, both of Bedford, England

[73] Assignee: Ares-Serono Research & Development Limited Partnership, Boston, Mass.

[21] Appl. No.: 240,478

[22] PCT Filed: Jun. 12, 1985

[86] PCT No.: PCT/GB85/00259

§ 371 Date: Feb. 7, 1986

§ 102(e) Date: Feb. 7, 1986

[87] PCT Pub. No.: WO86/00141

PCT Pub. Date: Jan. 3, 1986

Related U.S. Application Data

[63] Continuation of Ser. No. 6/834,247, Feb. 7, 1986, abandoned.

[30] Foreign Application Priority Data

Jun. 13, 1984 [GB] United Kingdom ............... 8415018
Jun. 13, 1984 [GB] United Kingdom ............... 8415019

[51] Int. Cl.⁵ .......................................... G01N 21/01
[52] U.S. Cl. ...................... 422/58; 156/61;
204/403; 350/96.3; 356/244; 356/440;
422/82.11; 422/102; 427/2; 435/7; 435/288;
435/301; 435/311
[58] Field of Search ............. 422/101, 102, 68, 58,
422/82.11; 435/288, 301, 311, 817, 7; 204/403;
427/2; 356/244, 440; 250/227; 350/96.3;
156/61

[56] References Cited

U.S. PATENT DOCUMENTS

| | | | |
|---|---|---|---|
| 4,050,895 | 9/1977 | Hardy et al. | 422/98 X |
| 4,327,073 | 4/1982 | Huang | 435/7 X |
| 4,447,546 | 5/1984 | Hirschfeld | 422/57 X |
| 4,582,684 | 4/1986 | Vogel | 422/57 |
| 4,591,550 | 5/1986 | Hafeman et al. | 204/1 T X |
| 4,654,532 | 3/1987 | Hirschfeld . | |
| 4,880,752 | 11/1989 | Keck et al. . | |

FOREIGN PATENT DOCUMENTS

| | | |
|---|---|---|
| 10456 | 4/1980 | European Pat. Off. . |
| 34049 | 8/1981 | European Pat. Off. . |
| 42755 | 12/1981 | European Pat. Off. . |
| 103426 | 3/1984 | European Pat. Off. . |
| 2325920 | 4/1977 | France . |
| 2090659 | 7/1982 | United Kingdom . |

OTHER PUBLICATIONS

Chabay, Analytical Chemistry, 54 (9), pp. 1071(A)–1080(A).

Primary Examiner—Robert J. Warden
Assistant Examiner—Jill Johnston
Attorney, Agent, or Firm—Cushman, Darby & Cushman

[57] ABSTRACT

A specifically-reactive sample-collecting and testing device possessing a cavity or cavities each having a dimension small enough to enable sample liquid to be drawn into the cavity by capillary action, wherein a surface of the cavity carries an immobilized reagent appropriate to the test to be carried out in the device, and wherein said surface is a surface of a transparent solid plate to act as a light-transmissive waveguide and forming a wall of the cavity, said plate having an edge which is substantially optically smooth and transverse to the plane of the plate.

39 Claims, 3 Drawing Sheets

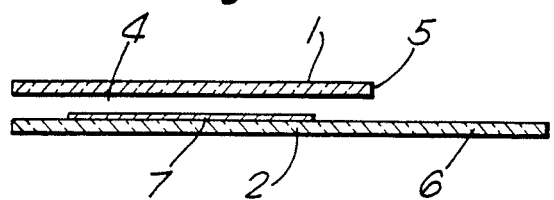
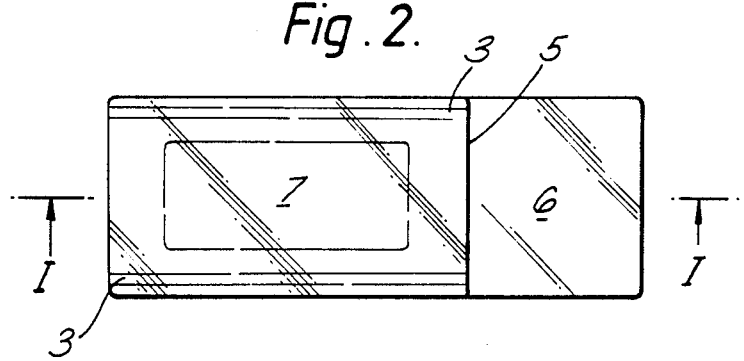
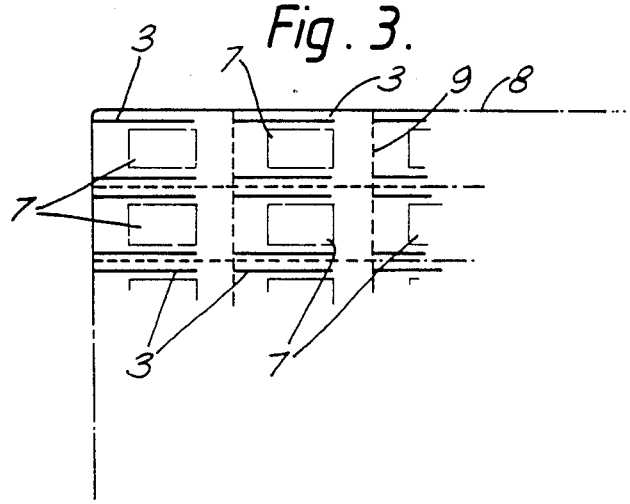

DEVICES FOR USE IN CHEMICAL TEST PROCEDURES

This invention relates to devices for use in chemical (especially biochemical or clinical) test procedures, to processes for their manufacture, and to the uses of the devices.

The devices are, in certain embodiments, intended for use in specific binding assay procedures, among which an important group is constituted by immunoassay procedures. Examples of such immuno assays, especially enzyme-linked immunoassays, are cited in Specifications Nos. EP 0 042 755, GB 2 074 727, GB 2 086 041, and GB 1 548 741.

Previously, immunoassay procedures have often been carried out using so-called microtitre wells, conventionally of about 0.5 ml working capacity, amongst a variety of other liquid containers for the assay reaction liquids. Other devices and arrangements for handling immunoassay materials are described in Specifications Nos. EP 0 31 993, GB 1 571 872, GB 1 584 129 and GB 1 414 479, for example.

In particular, the prior art contains numerous disclosures of analytical devices for handling and metering small volumes of test samples.

GB 2 090 659 (Instrumentation Laboratory, Inc.) describes test strips constructed with a self-filling metering channel and a lip or inlet on which a sample of more than about 10 microliters of for example whole blood can be placed, so that (for example) 10 microliters is taken up by capillary action to react with a reagent carried on a fibrous pad above a filter layer beneath a transparent window. The result can be viewed by the unaided eye, e.g. as a colour reaction.

GB 2 036 075 (H E Mennier), GB 1 104 774 (J P Gallagher), EP 0 057 110, 0 034 049, 0 010 456 (Kodak), all describe some other aspect of the uses of capillary channel or chamber dimensions for handling biological or test fluids.

GB 1 530 997 (Monsanto) describes the use of coated optical fibres which can be used in tests that change the light transmitting capabilities of the waveguides via reactions of the coatings, e.g. antigen-antibody reactions. WO 81/00912 (Buckles) also describes fibre-optic devices in which the fibre surface or surroundings modify the light transmission through the core.

USP 3 939 350 describes optical measurement of fluorescent material bound to the surface of a solid transparent prism by a method involving a single total internal reflection and interaction of the evanescent wave at the surface of the prism with the bound material.

EP 0 075 353 (Battelle) makes specific reference to the exponentially-decaying (evanescent) external radiation due to light which is propagated longitudinally in a fibre, and its interaction with coatings, and this principle is also taken up in the immunoassay test devices of EP 0 103 426 (Block) in which light of fluorescence excitation as well as emission wavelengths is propagated within a antigen—or antibody—coated optical fibre or plate contacting a capillary-dimensional sample liquid volume bounded by a tube or another plate and containing a fluorescent-tagged binding partner of the material coated on the fibre or plate.

According to the invention to be described here, capillary fill cell devices which can be conveniently manufactured, are provided to facilitate in particular specific binding assays using very small liquid samples.

According to the invention we provide a specifically-reactive sample-collecting and testing device possessing a cavity or cavities each having a dimension small enough to enable sample liquid to be drawn into the cavity by capillary action, wherein a surface of the cavity carries an immobilised reagent appropriate to the test to be carried out in the device, and wherein said surface is a surface of a transparent solid plate to act as a light-transmissive waveguide and forming a wall of the cavity, said plate having an edge which is substantially optically smooth and transverse, e.g. at some transverse angle but most preferably perpendicular, to the plane of the plate.

The devices enable convenient sample collection and carrying out optical analysis in situ of the products of reaction of the sample with reagent(s) contained in the devices. The waveguide plate can be transparent to infrared, visible, and/or ultraviolet light, and one method of using the devices is to arrange for a fluorescent material to become bound to the immobilised reagent to a variable extent depending on the assay and the sample material of interest, and then to carry out optical measurement of the resulting bound fluorescent material.

The immobilised reagent in the device can for example be an immobilised antigen or antibody which is capable of binding a fluorescent or luminescent or coloured component of an assay mixture. But it is understood that any immobilised material can be used that specifically interacts with another component of a test reaction material in a way that gives optically measurable results, depending only on the kind of test in question.

The surface of the cavity opposite to the reagent-bearing waveguide surface can, as in examples illustrated below, be formed of a second similar transparent plate. However, this is not necessary, and for some forms of test it may be suitable to use a light-absorbing or opaque opposite wall to the capillary cavity.

In some useful examples of the devices of this invention, a selective barrier such as a filter or dialysis membrane can be fitted to ensure that the takeup of sample liquid into the capillary-dimension cavity is selective to exclude unwanted material Such unwanted material will depend on the nature of the test but may include cells such as blood cells, cell debris or dispersed high-molecular-weight material A suitable filter can be for example a paper filter located at the sample entrance to the capillary cavity or a strip or area of filter or dialysis membrane material fixed at or in the capillary cavity.

It is also within the scope of the invention that the area covered by an immobilised reagent within the capillary cavity, e.g. an immobilised antigen or antibody, can be significantly less than the whole area of the capillary cavity, and arranged so that all of the sample liquid must pass over the immobilised reagent as liquid is drawn into the cavity. In this way a sample-concentration effect can be achieved, with a resulting surface concentration of relevant analyte material (e.g. complementary antibody or antigen) higher than would result from uniform adsorption over the whole capillary cell area. Such an immobilised coating over a restricted threshold area of the capillary cell surface can form in effect a selective barrier to allow passage of sample liquid beyond the barrier with selective retention of an analyte material of interest.

In the use of devices according to the invention, a drop of sample liquid can be placed on a collection surface of the test device, or else the device can be dipped into a quantity of liquid to be sampled. If ancillary reagents are needed they can be dosed separately, or they can be carried in dry releasable form on a part of the device to be contacted in use by sample liquid, eg. a surface of the capillary cavity or a surface of a filter if present.

Further variants and particular features of the test devices are described for example below.

According to the present invention we also provide a method of manufacturing specifically-reactive sample-collecting and testing devices, comprising the steps of (a) forming an immobilised specifically-reactive coating on the surface of a sheet material which is to provide part of a multiplicity of the devices, (b) forming an additional structure which together with said coated sheet material provides for each device of the multiplicity of devices a cavity of capillary dimension for collecting and retaining by capillarity a volume of sample liquid in contact with the specifically-reactive coating, and (c) separating the sheet material into portions each providing one or a plurality of the sample-collecting and testing devices. In this process the specifically-reactive coating can be confluent or continuous or divided into a pattern, e.g. of discrete portions, e.g. as a 2-dimensional array of patches. Where such patches are formed they can be made for example either by first forming a continuous coating and then removing portions of it to leave the desired pattern, e.g. the array of discrete portions, or as a printed (for example screen-printed or flexographically-printed) array of patches.

The specifically-reactive coating can be an immobilised specific binding material such as a covalently bound antigen or antibody or derivative thereof, also possibly coated with a humectant, to form an immunosorbent, with specificity appropriate to a desired assay. The additional structure can for example be a further sheet material bonded to the first sheet material by suitable bonding adhesive, and spaced therefrom by a capillary space, e.g. less than about 1 mm, to allow uptake of sample liquid between the sheets by capillarity, preferably in a defined reproducible volume. Either or both sheets may be transparent to light with optically regular, generally smooth, surfaces. The separation of units can be achieved by scribing and breaking the sheet materials, e.g. of glass, siliceous or plastics material, and in the examples described below is carried out so as to leave an external loading surface to which sample liquid can be loaded or applied and from which it can be drawn onto the cavity of the device The external loading surface has preferably a capacity to contain or hold at least enough liquid (e.g. in the form of a drop of material spread out over the surface) to load the cavity fully.

The invention extends to the products of the methods described herein and to the use of those products.

In certain examples of devices according to the invention, the cavity of the device can be a thin planar cavity between two opposite walls forming a cell, and preferably cemented or made into an integral unit. In some cases, for example, the device can include a bonded structure of transparent plates similar to the structure of an unfilled liquid crystal display device as obtained as an intermediate stage in manufacture of liquid crystal displays.

Thus devices according to the invention include those possessing a (for example disposable) translucent or transparent capillary cell, which can be made by the methods described herein, for carrying out specific binding assays, comprising a pair of opposite transparent plates spaced less than about 1 mm apart, and sealed together to form an apertured liquid-retentive cell able to take up and retain by capillary action a (preferably defined) volume of (usually aqueous) liquid, and carrying on at least one of its internal surfaces a coating of (preferably immobilised) specific binding agent with a specificity appropriate to the assay to be carried out "Defined volume" means a volume that is determined substantially by the shape and configuration of the cell itself and not appreciably by the volume of sample if applied in excess.

It is important to have an accurately defined (parallel) cavity of capillary gap dimensions in the devices of this invention, but not so important that the total volume taken up by the capillary gap should be defined: the important parameter is rather the volume dosing per unit area of the optical reagent bearing surface of the waveguide, and this is achieved by an accurately defined parallel spacing of the opposite walls of the cavity in the device. The spacing is preferably within the broad range about 0.01 to 1 mm, eg. of the order of 0.1 mm, eg. 0.03–0.3 mm, as a compromise between too wide spacings leading to excessive diffusion time of materials in the sample across the gap to the reagent-bearing surface, and too narrow spacings which may collect too little sample.

Materials suitable to form the cavity are for example glass, eg. sheet soda glass about 1 mm thick, silicas and plastics sheet material, eg. acrylic plastics material.

Where plastics materials are used to form the capillary cells, they can for example be used in the form of precision mouldings, e.g. provided with spacers such as ridges to achieve controlled spacing of the component walls of the capillary cell cavities.

In some cases the cell has an outer surface portion or lip to which a quantity of sample sufficient to fill the cell can be applied and from which it can easily be made to run into the capillary cell by capillary action. Such a lip can easily be formed by an extension of one of the plates, outwardly beyond the cell aperture, for a distance sufficient to give a surface area large enough for convenient sample loading. It can also if desired be given a liquid-conductive shape, such as a groove or channel leading towards the capillary cell inlet An alternative form of inlet is one formed by an aperture in one wall of the capillary cell, e.g. a hole that exposes an area of opposite wall of the cell on to which a sample can be loaded. Selective barriers such as those described elsewhere herein, such as filters and dialysis membranes, can also be located in or adjacent to such inlet apertures, and may be pre-dosed with dry releasable reagents. It is especially convenient to incorporate these features in the plastics capillary cells, and in such cases precision-moulded apertures supplied in a moulded plastics sheet can provide the perpendicular optically flat ends of the capillary cells when the resulting assembly of plural capillary cells is separated into individual cell units.

Preferably the sealing of the cell can be achieved by using a line of epoxy resin, leaving an aperture, e.g. extending the resin along two opposite sides of a rectangular capillary cell, to give a filling aperture and a further aperture left to allow the exit of air from the capillary cell as it fills up. Suitably, the resin can comprise solid particles to ensure a desired spacing for the plates as they bed down on the resin. Particles such as substantially monodisperse ballotini (fine glass particles) of diameter about 100 micron or otherwise corresponding to the chosen capillary gap, or short glass fibre lengths of for example 8 micron diameter and 50-100 micron long (e.g. made by mortar-grinding of long glass fibre and exclusion of long residual fibres by sieving), are suitable to regulate small spacings of the order of the diameter of the ballotini or the fibres. Generally, spacings in the range 5 to 500 microns can be chosen, by way of non-limitative example. Fibres are preferred for very narrow gaps, as they are more easily obtainable in diameters less than about 50 micron than are monodisperse ballotini: ballotini are preferred for the wider gaps.

The specifically reactive agent can be chosen among any of those normally used for purposes of specific binding assay, especially antigens and antibodies. Suitable examples are antiglobulin antibody, or antibody specific to human apolipoprotein $A_1$ or B, or antisteroid antibody, eg. specific for oestrone-3-glucuronide or pregnanediol glucuronide, or non-immunological binding agents such as concanavalin A, or cibacrom blue. They can be applied to the glass or silica or plastics surface in any of the known in the art. For example, where it is desired to have a releasable reagent, it can be useful simply to coat and dry the reagent and sucrose onto the carrier surface, either simultaneously or successively. Where it is desired to immobilise the reagent onto the carrier surface, covalent binding and other immobiliation techniques can be utilized where desired in any of the ways mentioned in EP specification 0 014 530 (Unilever), and references cited therein, especially in the case of plastics materials, and in any of the ways mentioned in "Immobilised Enzymes for Industrial Reactors" (ed. Messing, Academic Press, 1975; especially Filbert, chap 3), or in for example USP 3 652 761 or GB 1 530 997, for a wide variety of carrier materials including siliceous materials such as glass and silica.

The format of immunoassays, especially e.g. fluoroimmunoassays, which can be carried out in these capillary cell devices corresponds to the known formats of other immunoassays of the prior art. For example, such an assay can be a competitive assay in which an antigen analyte competes for binding sites on a specific immunoadsorbent with a fluorescent competitor, e.g. a fluorescent-labelled antigen analogue. Alternatively, the analyte can be contacted with the immunoadsorbent in the absence of the fluorescent ligand and this reaction can be followed by contact between the treated immunoadsorbent and the fluorescent ligand, e.g. as it may be released in slow or delayed manner from a releasable coating. In a further alternative, a solution-phase competition assay can be carried out between an analyte and a solution-phase binding partner and fluorescent-labelled competitor, (e.g. soluble antibody and competitive fluorescent-labelled antigen), in the presence of an immobilised antiglobulin carried on the capillary cell surface to immobilise the antibody participating in the assay, e.g. after the formation of the mixture of labelled and unlabelled immune complex.

In a further alternative, a sandwich test or antiglobulin test can be carried out in which the immunosorbent and fluorescent ligand (e.g. both antibody, or in the antiglobulin test respectively an antigen and antiglobulin) both have specific affinity for the analyte (the antigen or antibody) under test.

In a further alternative, a more general ligand-binding reaction may be used, eg. an immobilised layer of concanavalin A, which competitively binds glucose and a fluorescently-labelled dextran, or a layer of a dye such as cibacrom blue, which specifically binds fluorescent and unlabelled albumin or other proteins Similarly, luminescent assays may be carried out using labels which participate in chemiluminescent or bioluminescent reactions, eg. luciferase or horseradish peroxidase.

Embodiments of the invention are illustrated for example by the accompanying FIGS. 1-4 and associated description.

FIG. 1 shows a diagrammatic section through a disposable capillary cell device according to one embodiment of the invention.

FIG. 2 shows a diagrammatic plan of the cell device of FIG. 1, and includes a line I—I to show the line of section of FIG. 1.

FIG. 3 shows in diagrammatic fragmentary plan an intermediate stage in the manufacture of a plurality of devices as of FIGS. 1-2.

Figure 3A:
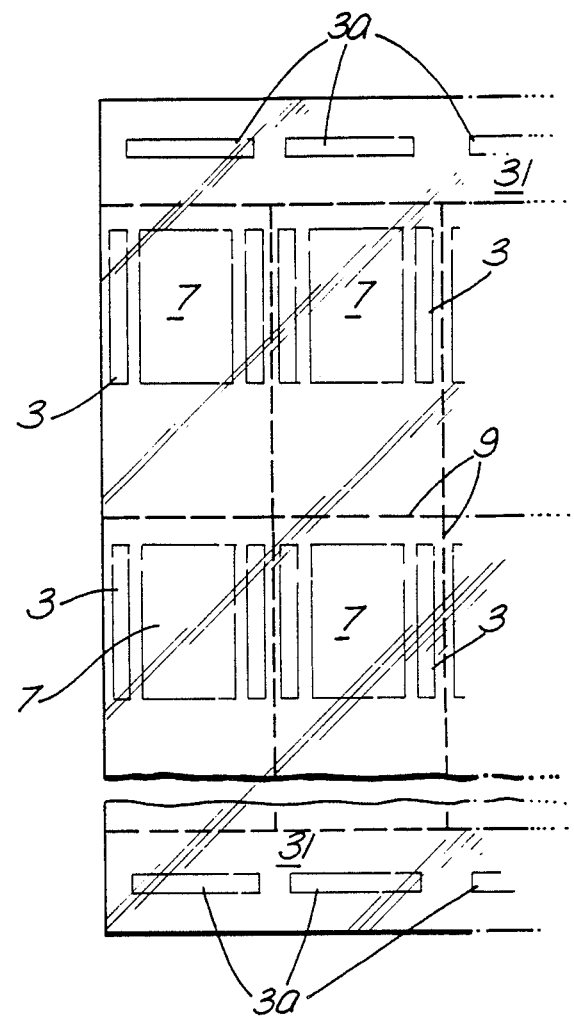
FIG. 3a is a schematic fragmentary plan corresponding to a variant on the arrangement shown in FIG. 3.

FIGS. 1-2 show a capillary cell device of a size to be handled easily, e.g. about 3 cm×1.5 cm. The device comprises upper transparent (e.g. plastics, glass, or silica) plate 1 and lower transparent (e.g. similar) plate 2 (about 1 mm thick) fixed together in parallel opposed and spaced relation, less than 1 mm apart, by bonding tracks 3 of suitable (e.g. epoxy) adhesive to form a capillary cell cavity 4, open at both ends, which communicates with the outside through a first discontinuity in the bonding 3 arranged to form a cell aperture at side 5 of plate 1. Another discontinuity is present at the other end of bonding 3, to leave another aperture, to allow exit of air when a sample liquid is loaded into the cell. Plate 2 is larger than plate 1 and has a portion 6 extending away from the aperture. Portion 6 of plate 2 acts as a platform or threshold or lip onto which a drop of sample liquid can be applied, so that this liquid can be made to fill the capillary cell cavity 4 by capillary flow. Cavity 4 attracts and contains a definite and adequately reproducible volume of liquid when loaded in this way.

Immobilised to the inner surface of the capillary cell is a layer 7 of material relevant to the test procedure in which the capillary cell is to be used. In the example shown in the drawings the layer 7 is a patch of material carried on plate 2. For the purpose of immunoassay, it can be for example an area of immobilised immunosorbent sensitisation, e.g. immobilised antibody, relevant to an immunoassay. There can be more than one such layer, e.g. a layer on plate 1 as well as plate 2, or a superimposition and/or side-by-side plurality of layers on either plate. For similar or other purposes, the layer 7 or other layer(s) lining the internal surface(s) of the capillary cell can include an electrically conductive layer or layers, as described in our copending application of even date, derived from UK 8415018, of June 13, 1984, and in such a case conductive external connections can be provided by means of conductive tracks or connectors from the interior of the cell to the exterior of the cell, if desired, passing between bonding layer 3 and the surface of the plates. These can for example be made in a manner known per se and used in the conventional surface fabrication of conductive tracks as often employed in the manufacture of semiconductors and liquid crystal displays, e.g. as referenced below When the cell is intended for making optical measurements, either plate 1 or plate 2 or both should be transparent or translucent The section shown as FIG. 1 presents plates 1 and 2 spaced apart because the line of section does not extend through the bonding tracks 3.

The fabrication of a plurality of cells such as that of FIGS. 1-2 is illustrated by FIG. 3, a fragmentary plan diagram showing an intermediate stage in the manufacture of such cells A large plate 8 of glass or other material to make plates 2 is cleaned and coated in any appropriate way (eg. as described below) with patches of material 7 of any of the kinds described above as well as tracks of bondable adhesive 3. A second plate, not shown, is then adpressed to plate 8, optionally after forming on it bonding tracks corresponding to track 3, and optionally after forming patches or tracks of any other desired material, and the adhesive is cured. Then the assembly is broken or cut along lines shown as dotted lines 9 in FIG. 3, and corresponding lines in the upper plate (not necessarily in registration with lines 9, though). The result is to give cells like the cells shown in FIGS. 1-2.

FIG. 3a shows in diagrammatic plan view an alternative and preferable intermediate stage in the manufacture of capillary cell devices as in for example FIGS. 1 and 2. The main differences between FIGS. 3 and 3a, apart from variation in shape and detail of pattern of the devices to be produced, are that waste edges 31 of the sheet material 8 are provided, and tracks of bondable adhesive 3a are provided in such waste edges 31. The purpose here is to achieve better or more convenient control of the spacing between the upper and lower plates: the bondable adhesive tracks 3 and 3a contain the fibres or microspheres described above to regulate spacing of upper and lower plates and the position of tracks 3a helps to avoid irregularity of spacing at the plate edges.

The arrangements of FIGS. 3 and 3a have been described in relation to the use of sheet glass as a substrate material: especially but not exclusively where plastics sheet is used, it can be convenient to use other than plain sheet material, e.g. the spacer ridges, inlet apertures and filter arrangements described elsewhere herein can be incorporated as part of such sheets before the capillary cells are assembled.

The capillary cell device of FIGS. 1-2, among other devices made according to this invention, can if desired be provided with any convenient form of handling-piece or holder and for this purpose may be provided with any convenient form of fixed or releasable connexion arrangement to engage with such a holder where this is not formed in one piece with the cell device.

For convenience of optical measurement, it is desirable that one or more edges of plate 1 and/or 2 are made substantially optically smooth and perpendicular to the plane of the plate. The remaining edges may if desired be coated with black paint or other light-absorbing material. Alternatively or additionally, absorbing pigment such as carbon black may be incorporated in the cement such as epoxy that is used to bond the two plates together In use, the device of FIGS. 1 and 2 can transmit fluorescence from an adsorbed fluorescent material along either or both of the plates 1 and 2 in the manner of a waveguide or optical fibre. Transfer of useful light across the boundary of the plate can occur by the evanescent wave located very close to the interface If desired, a thin layer of for example silica or magnesium fluoride, of the order of a quarter-wavelength thick at the wavelength of interest, may be fabricated on to the plate before deposition of the biochemical reagent, in order to improve light transfer across the boundary The thickness and refractive index of the dielectric layer are preferably together chosen to maximise the intensity of the evanescent wave associated with light transmitted in the plate in a path that corresponds to total internal reflection near (and slightly above) the critical angle for the boundary between the plate material and the sample liquid, e.g. usually in the range about 1°-5° above the critical angle. The optimum refractive index of the dielectric layer is as close as possible to that of the sample liquid: practically it is most usual to choose a dielectric of magnesium fluoride (n=1.38) or silica (n=1.46) when glass is used. The optimum thickness for the layer is expressed in terms of the angle of incidence P of the light in the plate at the plate-dielectric interface, and the refractive indices of the media: $n_1$ of the sample liquid, $n_2$ of the plate, $n_3$ of the dielectric L is the wavelength of the light in use:

$$t = L/4 \cdot \frac{\left[1 - 2/\pi \arccos\sqrt{\left(\frac{n_3^2 - n_2^2\sin^2 P}{n_3^2 - n_1^2}\right)}\right]}{\sqrt{(n_3^2 - n_2^2\sin^2 P)}}.$$

In further derived alternative examples, continuous or discontinuous thin metal layers e.g. of silver or indium, preferably overlain by a vacuum-deposited very thin corrosion-resisting layer such as silica, may also be deposited on either or both plates to enable the device to be used in corresponding other methods of optical analysis known in themselves, which exploit such layers, e.g. the per se known phenomenon of surface plasmon resonance, as described in B. Liedberg et al, Sensors and Actuators, 4 (1983) 299-304. In any of these cases the immobilised layers of biochemical reagents may be supplemented or replaced by releasable reagent coatings, e.g. formed by air-drying protein-sucrose mixtures in thin films on the plates: selected and combined according to the particular test chemistry to be performed in the device. The range of chemical or binding reactions that can form part of the tests to be carried out spans the range of known binding-reaction tests, and includes enzyme-linked, fluorescence, luminescence, binding and quenching reactions of any kind based on solid-phase immunoadsorbent or other specific binding adsorbent.

Further details of procedures and material to fabricate cell devices such as the capillary cell device of FIGS. 1-2 are given in the following Example, further illustrating embodiments of this invention.

EXAMPLE

A sheet of (e.g. soda) glass for example about 1 mm thick, and large enough to contain a 2-dimensional array of cell areas, with a plurality of several cell units in each direction, is cleaned by any suitable method, eg. by detergent and ultrasonic treatment and if need be by solvent vapour degreasing in known manner, or by successive hot (80° C.) treatments with ammonia hydrogen peroxide and hydrochloric acid/hydrogen peroxide, water-rinsing and airdrying, e.g. at 115° C. for 30 minutes. A pattern of patches of a desired protein or other coating is then applied by the following or equivalent technique. Covalent coupling of antigen or antibody or other protein is achieved by first reacting the glass with a silane-based coupling compound in known manner. A suitable such reagent is for example, as used here, a terminal amino-alkyl trimethoxysilane, e.g. the 3-aminopropyl compound, used at a concentration of suitably about 2% v/v in acetone. In alternative methods, another reagent substantially as described in USP 3 652 761 can be used instead After reaction with the amino-silane reagent, the amino terminals immobilised on to the flass are in turn reacted with (e.g. 2% pH 7) glutaraldehyde, excess reagents are removed and the activated glass with immobilised aldehyde groups is reacted with the protein in solution (e.g. 1 mg/ml antibody immunoglobulin), according to component techniques well known in themselves. Other proteins can be applied at choice in concentrations of the order of 0.1-1 mg/ml. Treatment at about pH 9.5 for 2 hours at 37° C. has been found suitable here. A suitable final active protein loading rate on the glass surface can be for example about 0.5 microgram/cm$^2$. This is thought to constitute a continuous or near-continuous layer. The dosage or density or specific activity of the immobilised layer is determined by the sensitivity requirements of the particular assay chemistry, which in itself forms no part of this invention. Excess reagents can be removed for example washing in strong buffer (0.1M acetate, 0.5M NaCl pH4-5), then neutral buffer washing, (pH 7-7.4), followed by pH 9-10 washing and neutralisation, e.g. with neutral tris buffer.

An alternative and sometimes preferred method for coupling protein to glass employs an epoxy-silane reagent, especially the glycidyloxypropyltrimethoxysilane (e.g. 2% v/v in toluene, 70° C. for 2½hours), according to DP Herman et al., J.Chromatogr.Sci., (1981), 19 (9) 470-6. With this reagent the use of aldehyde reagents can be omitted, as the epoxysilylated glass can react directly with protein.

It is usually desirable to apply a stabilising coating to such layer-coated surfaces such as a coating of a solid humectant such as sucrose. A suitable example of such a coating is an 8 micron-thick solid sucrose coating applied for example by spin-coating the plate with sucrose solution and drying in air.

Releasable coatings can be applied with per se known composition, e.g. carried in admixture with a solid humectant, such as sucrose glaze. We find that it can be desirable to include detergent or inert protein in such coatings (or a soluble salt or buffer material) especially where the active material to be released is itself a protein, and it can be especially desirable to avoid large excess of the reagents in such releasable coatings in relation to the test reactions in which they are to take part.

Uniformity of the coating processes can be important, and if appropriate can be checked by test procedures in which radiolabelled and/or fluorescent protein is coated, and then optionally reacted with a further and preferably differently-labelled binding agent. Uniformity of the coating and of its binding capacity can then be checked by surface fluorescent measurement and/or surface radioactivity measurement, eg. using a laboratory gamma-ray scanner.

If it is afterwards desired to etch the coating on the glass, the coated glass is then placed in a confined atmosphere substantially free of moisture or air draughts, e.g. it can be brought close to another flat inert surface to reduce the air gap on the coated side to about 1 mm or less. The glass is then illuminated with an ultraviolet patterned image (using preferably light of as narrow as practicable a waveband around c. 280 nm) in a pattern corresponding to areas from which the coating is to be etched away, e.g. a grid pattern, to leave a pattern of surviving protein patches. Illumination can for example be carried out using a GE 7-watt mercury lamp spaced a few centimeters from the plate, for a period of about 5-20 minutes. The illumination pattern can be produced by masking close to the plate, or by a real imaging system. The ultraviolet etching used here relies on the same principle as the u.v. etching process described by J A Panitz, I Giaver, in Surface Science, 97 (1980) pp 25-42, to which reference is made.

Then a uv-curable epoxy adhesive is printed on to the coated, eg. patch-coated, glass plate in a desired pattern for forming a connexion with an upper spaced plate. The epoxy adhesive is applied by a silk-screen technique which is conventional in itself, and in itself forms no part of this invention.

The epoxy resin can have a small content of short-length glass fibre, about 20 micron in diameter and about 100-200 micron long, (made for example by grinding long glass fibre in a mortar and sieving to remove residual long fibres). A preferred alternative to the glass-fibre pieces is a content of ballotini in the epoxy resin, used as follows. In order to produce a gap of for example 100 micron, correspondingly-sized ballotini are incorporated in the epoxy: a layer of epoxy a little thicker than the desired spacing between the plates, e g. 10% thicker, e.g. about 110 micron for a desired spacing of 100 micron, can be laid down by screen-printing, and the addition plate pressed gently into position to spread the epoxy slightly.

If desired, a mirror-image of the first pattern of epoxy adhesive can be applied as a pattern to a second similar sheet of glass, either coated patchwise with the same or a different protein or other coating material, or otherwise uncoated, and the two sheets then brought together, subjected to vacuum or deoxygenation if needed for curing, and cured by ultraviolet illumination. The ultraviolet is applied as an image with a pattern that avoids the patches of coated protein or other material which are to be retained in active form.

After adhesive curing, the two glass plates can be scribed and broken down into individual cell units in any convenient known manner as used in stages in the manufacture of liquid crystal devices, and in particular by the methods referred to in Specifications Nos. CH- 627 559, and 629 002, concerning fabrication of liquid crystal display devices. Corresponding steps in the methods of those specifications and of this invention can be performed by similar methods, mutatis mutandis.

A convenient form of cell obtainable by this process comprises two substantially parallel opposed layers of glass, air-spaced by about 5–500 micron, which, together with an incomplete frame of bonding material located between them, (having at least one opening for the inward passage of liquid and possibly also the outward passage of air), form a capillary cell able to take up a defined volume of aqueous liquid. Preferably one of the glass layers extends out beyond the opening of the cell to enable a drop of liquid to be placed on its surface and pass either wholly or partly into the cell.

Figure 4:
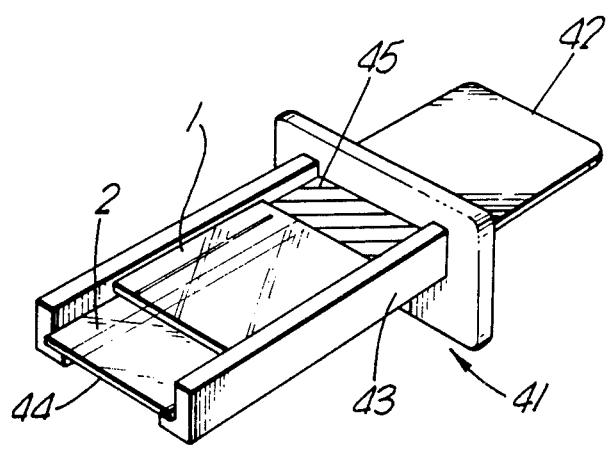
FIG. 4 shows in schematic perspective view a specifically-reactive capillary cell device according to an embodiment of invention.

FIG. 4 shows in schematic perspective a further example of a specifically-reactive capillary cell device according to an embodiment of the invention. The device shown is a disposable single-use test device for carrying out microchemical testing on very small liquid samples FIG. 5 (not to scale) shows a corresponding plan view and FIG. 6 a schematic section along lines 6'—6' in FIG. 5. The device of FIGS. 4–6 comprises an upper glass plate 1 and a lower glass plate 2 related as plates 1 and 2 of FIG. 1. A reactive layer as 7 in FIG. 1 is present on the surface of plate 2 but not shown in the drawings in FIGS. 4–6. If needed for the purposes of a particular test, an auxillary reagent can be provided as a releasable coating on the opposite wall of the cell, i.e. the surface of plate 1, so that the reagent dissolves in the sample liquid drawn into the cell The device of FIGS. 4–6 can be handled by the user by a handlepiece 42 of a supporting and handling frame indicated generally 41 and made of any convenient plastics moulded material Arms 43 serve to support the cell assembly and locate it in relation to the operative parts of an optical instrument for optical analysis of the contents of the sample cell End 44 of plate 2 is optically clear, flat and perpendicular to the plane of plate 2, to allow exit of light arising from the contents of the capillary cell between plates 1 and 2. The other edges of plates 1 and 2 are in this embodiment usefully painted black, and epoxy bonding tracks 3, corresponding to tracks 3 in FIG. 1, besides their content of 100 micron ballotini to space plates 1 and 2 apart, also contain carbon black granules to help minimise stray light A filter paper rectangle 45 is located on a part 46 of plate 2 that extends beyond the length of plate 1 to form a sample-receiving inlet the adjacent open end 47 of the capillary gap between plates 1 and 2 is an inlet for the capillary cell delimited by plates 1 and 2 and bonding tracks 3, and filter 45, of a grade sufficiently fine to exclude the passage of red blood cells, is in contact with open inlet end 47 and preferably slightly underlaps plate 2 at end 47. Filter 45 is retained in place if desired by adhesive along parallel lines continuing tracks 3, and can if desired be impregnated with a releasable/auxillary reagent such as for example a pH buffer salt. Portion 47 of plate 2 extending beyond plate 1 to the optical end 44 of plate 2 can if desired be given a hydrophobic coating.

In use, a sample of liquid to be tested, e.g. a drop of whole blood, can be applied to the inlet zone formed by filter 45, and from such a drop a quantity of relatively cell-free liquid is drawn into the capillary cell. Here take place the binding or other e.g. enzyme reactions appropriate to the nature of the required test and corresponding reagents previously carried in prepared dry form on one or both of the opposite internal cell walls formed by plates 1 and 2, and the loaded cell can then for example be put into a photometric instrument, e.g. that described in copending UK patent application Ser. No. 8415019, for optical measurement as described therein.

Figure 5:
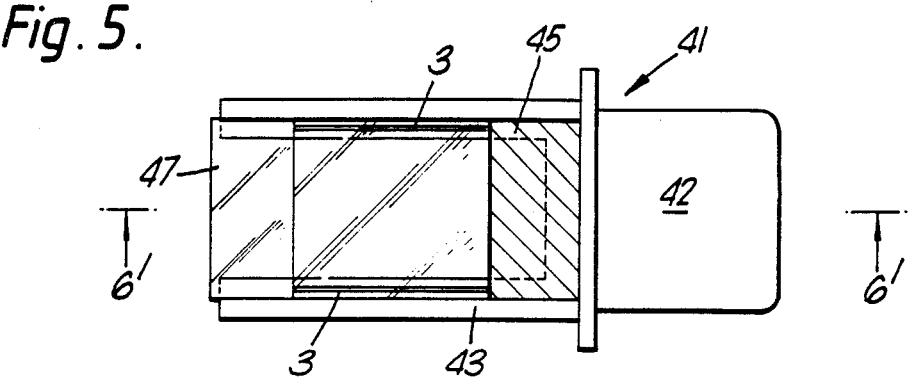
FIGS. 5 and 6 show a schematic plan and section of the device of FIG. 4.
Figure 6:
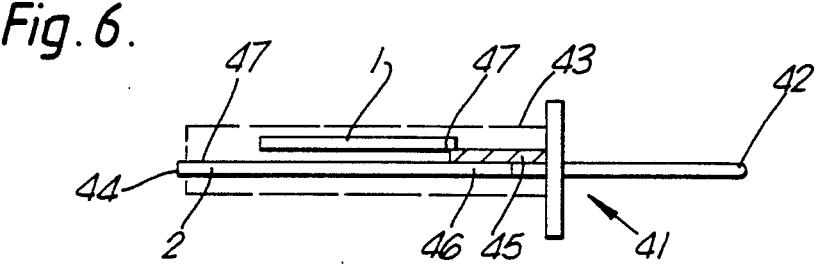
Figure 7:
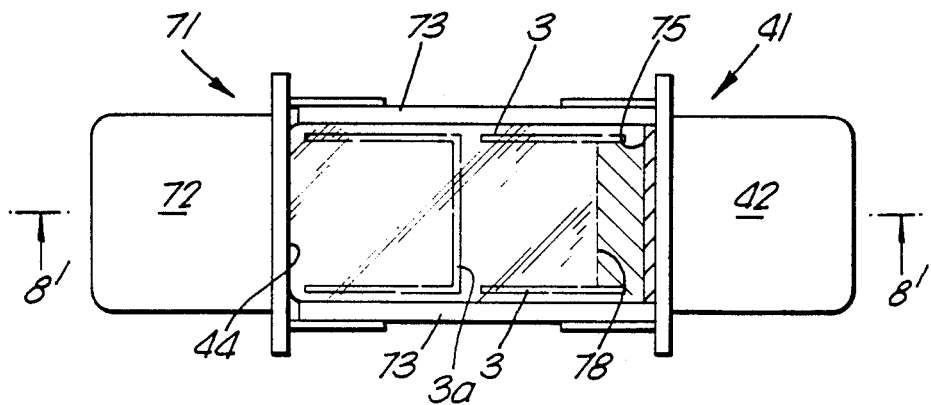
FIGS. 7 and 8 show a corresponding schematic plan and fragmentary section of an alternative device, a modification of the device of FIGS. 4-6.
Figure 8:
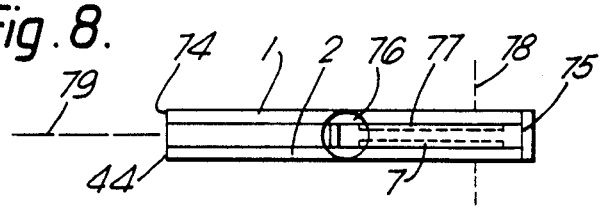

FIGS. 7 and 8 illustrate a modification of the device of FIGS. 4-6. The device has two snap-on handle-and-support pieces, one shown at 41, corresponding to 41 in FIGS. 46 except that it is detachable, and another handle and support piece 71 comprising handle 72, which is a removable snap-on fit over lateral ribs 73 at the optical end of the device, which comprises similar optical end-faces 44 and 74 of both the spaced-apart plates 1 and 2. Handle 42 is a firmer snap-on fit than handle 72.

The device of FIGS. 7 and 8 is supplied with handle 72 fitted and handle 42 separated. In this condition a cellulose nitrate or acetate microfine filter or dialysis membrane 75 is exposed at the inlet end of a capillary cell defined as before between plates 1 and 2 and binding tracks 3, but defined here also by a further transverse blackened epoxy bonding track 3a that limits the forward spread of liquid towards ends 44 and 74 of plates 1 and 2, and results in the forward parts of plates 1 and 2 being able to constitute waveguide portions bounded by air on each side. Two lateral gaps are left between tracks 3 and 3a and two corresponding apertures 76 in frame 73 allow for exit of air when the capillary cell fills with sample liquid. Thus, in use, the device can be held by handle 72 and dipped into a source of sample liquid to allow a sample to fill the capillary cell through filter 75. In this embodiment each of plates 1 and 2 carries an immobilised reactive layer 7 and 77 such as an appropriate antibody layer fabricated as described above. If desired, the extent of reactive layers 7 and 77 can be limited to the area shown hatched in FIG. 7 on each of plates 1 and 2 between filter 75 and line 78. With such an arrangement, the gently inflowing sample liquid passes over the reactive layers which are each able to abstract their respective ligand, the surface concentration of which can therefore be concentrated in the hatched region.

When the sample has been loaded, separate handle 42 can be snapped-on into place and the more weakly-attached handle 72 can be removed, thereby exposing the optical ends 44 and 74 of plates 1 and 2 for measurement as before, with the modification that two different optical properties may be measured at once by virtue of the separate optical waveguides 1 and 2 and different reactive layers 7 and 77 of the device. A corresponding optical measuring instrument therefore locates a diaphragm in a position shown by dotted line 79 to separate the respective lights emerging from plates 1 and 2.

The invention described herein is susceptible to many modifications and variations within its scope, and in particular extends to the use of any one or more of the singular and several features of the foregoing description and accompanying drawings and their equivalents.

Many of the devices made according to the above description can be applied to carry test samples which are to be measured optically by the photometric arrangements and methods described in our copending application derived from UK patent application Ser. No. 8415019 (June 13, 1984), the disclosure of which is hereby incorporated by reference with the present application.

We claim:

1. A sample collecting and testing device for use in the fluoroimmunoassay of an analyte present in sample liquid, said device comprising a planar capillary cell for the collection and retention of a volume of sample liquid to be tested therein, said capillary cell comprising a pair of flat, parallel plates fixed together with an air space therebetween and sealed along two opposite sides so as to provide fixed opposed inner surfaces defining a capillary cavity with a first aperture at one end thereof to allow uptake of sample liquid in the capillary cavity and a second aperture at the other end thereof to allow exit of air from the capillary cavity as it fills with sample liquid, wherein at least one of said plates is a light transmissive waveguide having an optically smooth edge which is transverse to the plane of the waveguide and perpendicular to the sealed sides thereof, said waveguide having bound to at least a portion of its inner surface, so as to be contacted by the sample liquid collected within the capillary cavity, an immobilised reagent capable of binding, either directly or indirectly, a fluorescent-labelled ligand, wherein said immobilised reagent and said fluorescent-labelled ligand is releasably retained within said device so as to be contacted by and released into the sample liquid collected therewithin.

2. A device according to claim 1 wherein the edges of the waveguide, except for said optically smooth edge, are coated with light-absorbing material.

3. A device according to claim 1 wherein interposed between the inner surface of the waveguide and the immobilised reagent bound thereto is a thin layer of dielectric material to enhance transfer of light across the surface of the waveguide by any fluorescent-labelled ligand which becomes bound to the immobilised reagent.

4. A device according to claim 3 wherein said dielectric material comprises magnesium fluoride or silica.

5. A device according to claim 1 wherein interposed between the inner surface of the waveguide and the immobilised reagent is a thin coating of conductive material capable of showing a surface plasmon resonance effect.

6. A device according to claim 5 wherein the thin coating of conductive material is a coating of silver up to about 50 nm thick.

7. A device according to claim 1 wherein the immobilised reagent is selected from the group consisting of an antigen, an antibody, a derivative of an antigen or an antibody, and a non-immunological binding agent.

8. A device according to claim 7 wherein the immobilised reagent is covalently bound to the inner surface of the waveguide.

9. A device according to claim 1 wherein at least one ancillary reagent is dry releasable form is coated on at least one of said inner surfaces.

10. A device according to claim 1 wherein the waveguide comprises a material selected from the group consisting of glass, silica and plastics material.

11. A device according to claim 1 further comprising a handling-piece or holder extending therefrom.

12. A device according to claim 1 further comprising conductive connections extending from the interior of the capillary cavity to the exterior of the device.

13. A device according to claim 1 wherein the optically smooth edge of said waveguide is perpendicular to the plane thereof.

14. A device according to claim 1 adapted to collect and retain a predetermined volume of sample liquid.

15. A device according to claim 1 wherein said immobilised reagent is positioned on the inner surface of said waveguide such that all of the sample liquid entering the capillary cavity must pass over it.

16. A device according to claim 1 wherein said fluorescent-labelled ligand is releasably coated onto at least one of said inner surfaces.

17. A device according to claim 16 wherein said fluorescent-labelled ligand is releasably coated onto the inner surface of the plate opposite said waveguide.

18. A device according o claim 1 further comprising a selective barrier-type filter located one of within and in the inlet path to, the first aperture of the capillary cavity such that sample fluid entering the capillary must pass through said selective barrier.

19. A device according to claim 18 wherein said fluorescent-labelled ligand is releasably retained within said selective barrier.

20. A device according to claim 1 wherein one of said plates extends longitudinally beyond the other of said plates so as to form a lip in communication with the first aperture of said capillary cavity so that sample liquid applied to said lip will enter the capillary cavity.

21. A device according to claim 1 wherein the immobilised reagent comprises a specific binding agent for the analyte to be assayed and wherein the fluorescent-labelled ligand has a specific affinity for one of the binding agent and the analyte and is releasably bound to at least one of said inner surfaces.

22. A device according to claim 21 wherein the plate opposite said waveguide has a light-absorbing surface.

23. A device according to claim 1 wherein the plate opposite said waveguide has a light-absorbing surface.

24. A device according to claim 23 wherein the edges of the waveguide, except for said optically smooth edge, are coated with light-absorbing material.

25. A process for manufacturing sample collecting and testing devices for use in the fluorescent or luminescent immunoassay of an analyte comprising the steps of (a) immobilizing a reagent appropriate to the test to be carried out in the device onto portions of the surface of a transparent flat sheet material which is capable of acting as a light-transmissive waveguide and which is to provide a part of a multiplicity of the devices, (b) attaching to said sheet material an additional flat sheet material in parallel, spaced relation thereto so as to provide for each device of the multiplicity of devices a capillary cavity sealed along two opposite sides thereof and containing said immobilised reagent on at least a portion of the inner surface thereof, said capillary cavity adapted for collecting and retaining by capillarity a volume of sample liquid in contact with said immobilised reagent and (c) separating the assembled sheets into portions, each portion providing one or a plurality of the sample collecting and test devices, such that the transparent sheet material of each device has at least one optically smooth edge transverse to the plane of the sheet and perpendicular to the sealed sides thereof.

26. A process according to claim 25 wherein the immobilised reagent is provided as a pattern of discrete patches.

27. A process according to claim 26 wherein the patches forming the pattern are made by first forming a continuous coating and then removing portions of it to leave the desired pattern of discrete patches.

28. A process according to claim 26 wherein said discrete patches of immobilised reagent are applied by printing.

29. A process according to claim 25 wherein the immobilised reagent is selected from the group consisting of an antigen, an antibody, a derivative of an antigen or an antibody, and a non-immunological binding agent.

30. A process according to claim 29 wherein prior to application of the immobilised reagent, a thin coating of conductive material capable of showing a surface plasmon resonance effect is applied to the surface of the transparent sheet material which is to carry said immobilised reagent.

31. A process according to claim 30 wherein the thin coating of conductive material is a coating of silver up to about 50 nm thick.

32. A process according to claim 29 wherein prior to application of the immobilised reagent a thin dielectric layer is deposited on the surface of the transparent sheet material which is to carry said immobilised reagent.

33. A process according to claim 32 wherein the thin dielectric layer comprises magnesium fluoride or silica.

34. A process according to claim 25 wherein prior to step (b) one or more ancillary reagents are applied in dry releasable form to portions of the surface of one of said flat sheet materials so as to become part of the inner surface of each device to be contacted in use by sample liquid.

35. A process according o claim 34 wherein at least one of the ancillary reagents is a fluorescent-labelled ligand appropriate to the test for analyte to be carried out in each device.

36. A process according to claim 35 wherein said immobilised reagent comprises a specific binding reagent for the analyte to be assayed in each device.

37. A process according to claim 36 additionally comprising coating a light-absorbing material onto a surface of said additional flat sheet material.

38. A process according to claim 25 wherein said additional flat sheet material is bonded to said transparent flat sheet material by means of intermittent strips of a suitable bonding adhesive, wherein said strips seal the sides of each device.

39. A sample collecting and testing device for use in the luminescent immunoassay of an analyte present in sample liquid, said device comprising a planar capillary cell for the collection and retention of a volume of sample liquid to be tested therein, said capillary cell comprising a pair of flat, parallel plates fixed together with an air space therebetween and sealed along two opposite sides so as to provide fixed opposed inner surfaces defining a capillary cavity with a first aperture at one end thereof to allow uptake of sample liquid in the capillary cavity and a second aperture at the other end thereof to allow exit of air from the capillary cavity as it fills with sample liquid, wherein at least one of said plates is a light transmissive waveguide having an optically smooth edge which is transverse to the plane of the waveguide and perpendicular to the sealed sides thereof, said waveguide having bound to at least a portion of its inner surface, so as to be contacted by the sample liquid collected within the capillary cavity, an immobilised reagent capable of binding, either directly or indirectly, a luminescent-labelled ligand, wherein said immobilised reagent and said luminescent-labelled ligand are appropriate to the test for analyte to be carried out in the device, and wherein said luminescent-labelled ligand is releasably retained within said device so as to be contacted by and released into the sample liquid collected therewithin.

* * * * *

UNITED STATES PATENT AND TRADEMARK OFFICE
CERTIFICATE OF CORRECTION

PATENT NO. : 4,978,503

DATED : December 18, 1990

INVENTOR(S) : SHANKS ET AL

It is certified that error appears in the above-identified patent and that said Letters Patent is hereby corrected as shown below:

In column 13, line 17, after "ligand", the phrase --are appropriate to the test for analyte to be carried out in the device, and wherein said fluorescent-labelled ligand-- should be inserted.

Signed and Sealed this

First Day of September, 1992

Attest:

DOUGLAS B. COMER

Attesting Officer

Acting Commissioner of Patents and Trademarks